(12) United States Patent
Moss

(10) Patent No.: US 11,191,817 B2
(45) Date of Patent: *Dec. 7, 2021

(54) TREATMENT OF INFECTION BY HUMAN ENTEROVIRUS D68

(71) Applicant: Ansun Biopharma, Inc., San Diego, CA (US)

(72) Inventor: Ronald B. Moss, Encinitas, CA (US)

(73) Assignee: AnsunBiopharma, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/858,514

(22) Filed: Apr. 24, 2020

(65) Prior Publication Data

US 2021/0052708 A1    Feb. 25, 2021

Related U.S. Application Data

(63) Continuation of application No. 16/450,946, filed on Jun. 24, 2019, now abandoned, which is a continuation of application No. 15/512,009, filed as application No. PCT/US2015/050798 on Sep. 17, 2015, now Pat. No. 10,328,128.

(60) Provisional application No. 62/192,439, filed on Jul. 14, 2015, provisional application No. 62/051,716, filed on Sep. 17, 2014.

(51) Int. Cl.
| | |
|---|---|
| *A61K 39/00* | (2006.01) |
| *A61K 38/46* | (2006.01) |
| *C12N 7/00* | (2006.01) |
| *A61K 38/16* | (2006.01) |
| *C07K 14/52* | (2006.01) |
| *C07K 14/54* | (2006.01) |
| *C07K 14/705* | (2006.01) |
| *C07K 14/81* | (2006.01) |
| *C07K 14/485* | (2006.01) |
| *C12N 9/24* | (2006.01) |

(52) U.S. Cl.
CPC ............ *A61K 38/46* (2013.01); *A61K 38/164* (2013.01); *C07K 14/485* (2013.01); *C07K 14/522* (2013.01); *C07K 14/5421* (2013.01); *C07K 14/70503* (2013.01); *C07K 14/8128* (2013.01); *C12N 7/00* (2013.01); *C12N 9/2402* (2013.01); *C12Y 302/01018* (2013.01); *C07K 2319/20* (2013.01); *Y02A 50/30* (2018.01)

(58) Field of Classification Search
CPC .................................................... A61K 38/46
See application file for complete search history.

(56) References Cited

U.S. PATENT DOCUMENTS

| | | | |
|---|---|---|---|
| 7,807,174 B2 | 10/2010 | Fang et al. | |
| 8,084,036 B2 | 12/2011 | Yu et al. | |
| 10,328,128 B2* | 6/2019 | Moss ................ | C07K 14/5421 |
| 2003/0124109 A1 | 7/2003 | Higuchi et al. | |
| 2005/0004020 A1 | 1/2005 | Yu et al. | |
| 2005/0112751 A1 | 5/2005 | Fang et al. | |
| 2007/0190163 A1 | 8/2007 | Malaknov et al. | |
| 2008/0075708 A1 | 3/2008 | Yu et al. | |
| 2010/0010018 A1 | 1/2010 | Makarov et al. | |
| 2017/0290893 A1 | 10/2017 | Moss | |

OTHER PUBLICATIONS

Belser et al., "DAS 181, a novel sialidase fusion protein, protects mice from lethal avian influenza H5N1 virus infection," J Infect Dis, Nov. 2007, 196(10):1493-1499.
Binford et al., "Conservation of amino acids in human rhinovirus 3C protease correlates with broad-spectrum antiviral activity of rupintrivir, a novel human rhinovirus 3C protease inhibitor," Antimicrob Agents Chemother, Feb. 2005, 49(2):619-626.
Bochkov et al., "Budesonide and formoterol effects on rhinovirus replication and epithelial cell cytokine responses," Respir Res, Oct. 2013, 14:98.
Brickelmaier et al., "Identification and characterization of mefloquine efficacy against JC virus in vitro," Antimicrob Agents Chemother, May 2009, 5(5)3:1840-1849.
Brown et al., "Seven Strains of Enterovirus D68 Detected in the United States during the 2014 Severe Respiratory Disease Outbreak," Genome Announc, Nov. 2014, 2(6). Pii::e01201-01214.
Collett et al., "A case for developing antiviral drugs against polio," Antiviral Res, Sep. 2008, 79(3):179-187.
De Palma et al., "Potential use of antiviral agents in polio eradication," Emerg Infect Dis, Apr. 2008, 14(4):545-551.
Furuta et al., "In vitro and in vivo activities of anti-influenza virus compound T-705," Antimicrob Agents Chemother, Apr. 2002, 46(4):977-981.
Gao et al., "Discovery of itraconazole with broad-spectrum in vitro antienterovirus activity that targets nonstructural protein 3A," Antimicrob Agents Chemother, May 2015, 59(5):2654-2665.
GenBank Accession No. D01045, "Micromonospora viridifaciens DNA for nedR protein and neuraminidase, complete cds," Dec. 18, 2007, 3 pages.
GenBank Accession No. NM080741, "*Homo sapiens* sialidase 4 (NEU4), transcript variant 1, mRNA," May 12, 2013, 4 pages.
GenBank Accession No. X87369, "C.perfringens nanH gene & ORF1,2,3 & 4," Apr. 18, 2005, 4 pages.
GenBank Accession No. Y16535, "*Homo sapiens* NEU2 gene," Feb. 11, 2000, 3 pages.

(Continued)

*Primary Examiner* — Albert M Navarro
*Assistant Examiner* — Mark Navarro
(74) *Attorney, Agent, or Firm* — Fish & Richardson P.C.

(57) ABSTRACT

The present disclosure provides compositions and methods for treating an infection by EV-D68. In particular, the present disclosure provides methods that entail administering agents having an anchoring domain that anchors the compound to the surface of a target cell, and a sialidase domain that can act extracellularly to inhibit infection of a target cell by EV-D68.

8 Claims, No Drawings

Specification includes a Sequence Listing.

(56) References Cited

OTHER PUBLICATIONS

Goger et al., "Different affinities of glycosaminoglycan oligosaccharides for monomeric and dimeric interleukin-8: a model for chemokine regulation at inflammatory sites," Biochem., Feb. 2002, 41(5):1640-1646.

Imamura et al. Antigenic and receptor binding properties of enterovirus 68. J Virol ePub Dec. 26, 2013 vol. 88 No. 5 pp. 2374-2384. Especially abstract, p. 2831 col. 1 para 4.

International Preliminary Report on Patentability for International Application No. PCT/US15/50798, dated Mar. 21, 2017, 6 pages.

International Search Report and the Written Opinion of the International Searching Authority for PCT/US15/50798 dated Dec. 21, 2015, 12 pages.

Lee et al., "Analysis of affinity and structural selectivity in the binding of proteins to glycosaminoglycans: development of a sensitive electrophoretic approach," Pro Natl Acad Sci USA, Apr. 1991, 88(7):2768-2772.

Liu et al., "Structure and inhibition of EV-D68, a virus that causes respiratory illness in children," Science, Jan. 2015, 347(6217):71-74.

Malakhov et al., "Sialidase fusion protein as a novel broad-spectrum inhibitor of influenza virus infection," Antimicrob. Agents Chemother., Apr. 2006, 50(4):1470-1479.

Meyer et al., "On the role of sialic acid in the rheological properties of mucus," Biochim Biophys Acta, Jun. 1975, 392(2):223-232.

Midgley et al., "Severe respiratory illness associated with enterovirus D68—Missouri and Illinois, 2014," MMWR Morb Mortal Wkly Rep, Sep. 2014, 63(36):798-799.

Monti et al., "Cloning and characterization of NEU2, a human gene homologous to rodent soluble sialidases," Genomics, Apr. 1999, 57(1): 137-143.

Monti et al., "Recent development in mammalian sialidase molecular biology," Neurochem Res, Aug. 2002, 27(7-8):649-663.

Moss et al., "A phase II study of DAS 181, a novel host directed antiviral for the treatment of influenza infection," J Infect Dis, Dec. 2012, 206(12): 1844-1851.

Oberste et al., "In vitro antiviral activity of V-073 against polioviruses," Antimicrob Agents Chemother, Oct. 2009, 53(10):4501-4503.

Pevear et al., "Activity of pleconaril against enteroviruses," Antimicrob Agents Chemother, Sep. 1999, 43(9):2109-2115.

Potier et al., "Fluorometric assay of neuraminidase with a sodium (4-methylumbelliferyl-alpha-D-N-acetylneuraminate) substrate," Anal. Biochem., Apr. 1979, 94(2):287-296.

Rhoden et al. In vitro efficacy of antiviral compounds against 1 enterovirus D68. Anlimicrob. Agents Chemother [accepted manuscript posted online] ePub Sep. 14, 2015 pp. 1-13. Especially p. 4 para 3, p. 6 para 2, p. 12 table 1.

Rhoden et al., "Anti-poliovirus activity of protease inhibitor AG-7404, and assessment of in vitro activity in combination with antiviral capsid inhibitor compounds," Antiviral Res, May 2013, 98(2):186-191.

Rossignol, "Nitazoxanide: a first-in-class broad-spectrum antiviral agent," Antiviral Res, Oct. 2014, 110:94-103.

Schieble et al., "A probable new human picornavirus associated with respiratory diseases," Am J Epidemiol, Mar. 1967, 85(2):297-310.

Strating et al., "Itraconazole Inhibits Enterovirus Replication by Targeting the Oxysterol-Binding Protein," Cell Reports, Feb. 2015, 10(4):600-615.

Thibaut et al., "Combating enterovirus replication: State-of-the-art on antiviral research," Biochem Pharmacol, Jan. 2012, 83(2):185-192.

Ulferts et al., "Selective serotonin reuptake inhibitor fluoxetine inhibits replication of human enteroviruses B and D by targeting viral protein 2C," Antimicrob Agents Chemother, Apr. 2013, 57(4): 1952-1956.

Weisgraber et al., "Human apolipoprotein E. Determination of the heparin binding sites of apolipoprotein E3," J Bio Chem, Feb. 1986, 261(5):2068-2076.

Witt et al., "Differential binding of chemokines to glycosaminoglycan subpopulations," Curr Bio, May 1994, 4(5):394-400.

\* cited by examiner

TREATMENT OF INFECTION BY HUMAN ENTEROVIRUS D68

This application is a continuation and claims priority to U.S. application Ser. No. 16/450,946 filed Jun. 24, 2019, which is a continuation and claims priority to U.S. application Ser. No. 15/512,009, filed Mar. 16, 2017, which is a U.S. National Phase Application under 35 U.S.C. 371 of International Patent Application No. PCT/US2015/050798, filed Sep. 17, 2015, which claims the benefit of U.S. Provisional Patent Application Ser. Nos. 62/192,439, filed Jul. 14, 2015, and 62/051,716, filed on Sep. 17, 2014. The entire contents of each of the foregoing applications are hereby incorporated by reference.

BACKGROUND

Human enterovirus D68 (EV-D68) (species, *Human enterovirus* D; genus, *Enterovirus*; family, Picornaviridae) can cause severe respiratory tract infections. It was rarely identified in patients in the United States prior to about 2005. However, since the late 2000s, the number of reported EV-D68 cases increased dramatically in in various countries. Some EV-D68 infections are characterized by severe disease, requiring intensive care and non-invasive ventilatory support. A 2014 EV-D68 outbreak particularly affected children with a history of asthma or reactive airway disease; and exacerbation of pre-existing asthma or reactive airway disease, similar to that associated with rhinovirus (RV) infection was noted in a high proportion of cases, though some patients with no history of asthma also had asthma-like symptoms (Midgley et al., 2014. *MMWR Morb Mortal Wkly Rep* 63:798-799).

SUMMARY

The present disclosure provides compositions and methods for treating EV-D68 infection and disorders associated with EV-D68 infection. Specifically, it provides compounds which can act extracellularly to reduce (e.g., reduce the risk of) or prevent infection of a cell by EV-D68 and method of treatment employing such compounds. Some preferred embodiments of the disclosure include therapeutic compounds having an anchoring domain that facilitates association of the compound with the surface of a target cell and a sialidase domain that can act extracellularly to reduce or prevent infection of the target cell by a pathogen, such as a virus. In some embodiments the compound comprises, consists of or consists essentially all or a catalytically active portion of a sialidase. In some embodiments, the methods comprise administering a capsid inhibitor (e.g., pleconaril, pocapavir orvapendavir) and a composition comprising DAS181.

Thus, described herein are methods of treating an infection by EV-D68 or an EV-D68 associated disorder in a patient, the method comprising administering to the patient a therapeutically effective amount of an agent having sialidase activity. In various embodiments: the patient is immunocompromised; the patient is undergoing immunosuppressive therapy; the patient is over age 70; the patient is under age 18; the patient is under age 10; and the agent having sialidase activity is a polypeptide comprising a portion of a sialidase having sialidase activity. In some cases, the polypeptide comprises or consists of a fusion protein wherein the fusion protein comprises at least a first portion comprising a portion of a sialidase having sialidase activity and the second portion binds to a glycosaminoglacan (GAG). In some cases, the polypeptide comprises or consists of a fusion protein comprising at least a first portion comprising a portion of a sialidase having sialidase activity and the second portion has a net positive charge at physiological pH. In some cases, the portion that binds to a GAG is selected from the group comprising: human platelet factor 4 (SEQ ID NO: 2), human interleukin 8 (SEQ ID NO: 3), human antithrombin III (SEQ ID NO: 4), human apoprotein E (SEQ ID NO: 5), human angio associated migratory protein (SEQ ID NO: 6), and human amphiregulin (SEQ ID NO: 7). In some cases, the agent having sialidase activity is a bacterial sialidase (e.g., the bacterial sialidase is selected from a group comprising: *Vibrio cholera, Arthrobacter ureafaciens, Clostridium perfringens, Actinomyces viscosus*, and *Micromonospora viridifaciens*). In some cases, the agent having sialidase activity is a human sialidase.

In one aspect, the disclosure provides a method for treating infection by EV-D68. In preferred embodiments, the method comprises administering an agent having sialidase activity, such as a sialidase or a fragment thereof containing a sialidase catalytic domain, including a sialidase catalytic domain fusion protein, to a subject to treat an infection. A pathogen can be, for example, a viral pathogen. The method includes administering a pharmaceutically effective amount of an agent of the present disclosure to at least one target cell of a subject. Preferably, the pharmaceutical composition can be administered by the use of a topical formulation.

In some cases the agent includes a glycosaminoglacan (GAG) binding domain. The GAG binding domain can be all or a fragment of: human platelet factor 4, human interleukin 8, human antithrombin III, human apoprotein E, human angio associated migratory protein, or human amphiregulin.

The source of the sialidase activity can be bacterial or human. In preferred embodiments, the bacterial source of the sialidase is selected from *Vibrio cholera, Arthrobacter ureafaciens, Clostridium perfringens, Actinomyces viscosus*, and *Micromonospora viridifaciens*.

In some embodiments, administration of the agent having sialidase activity leads to an improvement in one or more symptoms of the infection and/reduces viral load.

In some cases the agent is administered to the lung, e.g., by inhalation.

In some cases, the agent having sialidase activity is DAS181. In some cases the method comprises administering composition comprising DAS181 or microparticles comprising DAS181.

In some cases the composition further comprises a capsid inhibitor (e.g. pleconaril, pocapavir orvapendavir).

DETAILED DESCRIPTION

In general, the present disclosure relates to methods for treating EV-D68 infection using agents having sialidase activity. Suitable agents are described in U.S. Pat. Nos. 8,084,036 and 7,807,174 which are both hereby incorporated by reference in their entirety. The agents having sialidase activity can remove sialic acid residues from the surface of cells and reduce infection by certain viruses.

In some embodiments, the severity of the infection is reduced with the treatment of the compounds. The reduction of the severity of the infection can be measured by the reduction of one or more symptoms which present with the infection.

The compounds of the present disclosure have sialidase activity. In some instances, the compounds having sialidase activity are a fusion protein in which the portion having sialidase activity is fused to a protein or protein fragment not having sialidase activity. In some instances the portion having sialidase activity is fused to an anchoring domain. In some instances the anchoring domain is GAG.

DAS181 (SEQ ID NOs: 15 and 16) is a fusion protein compound comprising the catalytic domain of a sialidase (*A. viscous*) and an anchoring domain that is a human amphiregulin GAG-binding domain. In some instances of the present disclosure, DAS181 could be used to treat (and/or reduce the risk of) infection by EV-D68 and disorders associated therewith.

In some cases the compound having sialidase activity comprises, consists of or consists essentially of all or a portion of the catalytic domain of a sialidase such as *A. viscous* sialidase.

Unless defined otherwise, all technical and scientific terms used herein have the same meaning as commonly understood by one of ordinary skill in the art to which this disclosure belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

A "target cell" is any cell that can be infected by EV-D68, such as a lung cell.

A "domain that can anchor said at least one sialidase domain to the membrane of a target cell", also called an "extracellular anchoring domain" or simply, "anchoring domain" refers to a moiety that can interact with a moiety that is at or on the exterior of a cell surface or is in close proximity to the surface of a cell. An extracellular anchoring domain can be reversibly or irreversibly linked to one or more moieties, such as, preferably, one or more sialidase domains, and thereby cause the one or more attached therapeutic moieties to be retained at or in close proximity to the exterior surface of a eukaryotic cell. Preferably, an extracellular anchoring domain interacts with at least one molecule on the surface of a target cell or at least one molecule found in close association with the surface of a target cell. For example, an extracellular anchoring domain can bind a molecule covalently or noncovalently associated with the cell membrane of a target cell, or can bind a molecule present in the extracellular matrix surrounding a target cell. An extracellular anchoring domain preferably is a peptide, polypeptide, or protein, and can also comprise any additional type of chemical entity, including one or more additional proteins, polypeptides, or peptides, a nucleic acid, peptide nucleic acid, nucleic acid analogue, nucleotide, nucleotide analogue, small organic molecule, polymer, lipids, steroid, fatty acid, carbohydrate, or a combination of any of these.

As used herein, a protein or peptide sequences is "substantially homologous" to a reference sequence when it is either identical to a reference sequence, or comprises one or more amino acid deletions, one or more additional amino acids, or more one or more conservative amino acid substitutions, and retains the same or essentially the same activity as the reference sequence. Conservative substitutions may be defined as exchanges within one of the following five groups:

I. Small, aliphatic, nonpolar or slightly polar residues: Ala, Ser, Thr, Pro, Gly II. Polar, negatively charged residues and their amides: Asp, Asn, Glu, GIn III. Polar, positively charged residues: His, Arg, Lys IV. Large, aliphatic nonpolar residues: Met, Leu, Ile, Val, Cys V. Large aromatic residues: Phe, Try, Trp Within the foregoing groups, the following substitution are considered to be "highly conservative": Asp/Glu, His/Arg/Lys, Phe/Tyr/Trp, and Met/Leu/Ile/Val. Semi-conservative substitutions are defined to be exchanges between two of groups (I)-(IV) above which are limited to supergroup (A), comprising (I), (II), and (III) above, or to supergroup (B), comprising (IV) and (V) above. In addition, where hydrophobic amino acids are specified in the application, they refer to the amino acids Ala, Gly, Pro, Met, Leu, Ile, Val, Cys, Phe, and Trp, whereas hydrophilic amino acids refer to Ser, Thr, Asp, Asn, Glu, GIn, His, Arg, Lys, and Tyr.

As used herein, the phrase "therapeutically effective amount" refers to the amounts of active compounds or their combination that elicit the biological or medicinal response that is being sought in a tissue, system, animal, individual or human by a researcher, veterinarian, medical doctor or other clinician, which includes one or more of the following:

(1) inhibiting the disease and its progression; for example, inhibiting a disease, condition or disorder in an individual who is experiencing or displaying the pathology or symptomatology of the disease, condition or disorder (i.e., arresting further development of the pathology and/or symptomatology) such as in the case of EV-D68 infection, and (2) ameliorating the disease; for example, ameliorating a disease, condition or disorder in an individual who is experiencing or displaying the pathology or symptomatology of the disease, condition or disorder (i.e., reversing the pathology and/or symptomatology) such as in the case of EV-D68 infection.

As used herein, the phrase "treating (including treatment)" includes one or more of the following:

(1) inhibiting the disease and its progression; for example, inhibiting a disease, condition or disorder in an individual who is experiencing or displaying the pathology or symptomatology of the disease, condition or disorder (i.e., arresting further development of the pathology and/or symptomatology), and (2) ameliorating the disease; for example, ameliorating a disease, condition or disorder in an individual who is experiencing or displaying the pathology or symptomatology of the disease, condition or disorder.

A "sialidase" is an enzyme that can remove a sialic acid residue from a substrate molecule. The sialidases (N-acylneuraminosylglycohydrolases, EC 3.2.1.18) are a group of enzymes that hydrolytically remove sialic acid residues from sialo-glycoconjugates. Sialic acids are alpha-keto acids with 9-carbon backbones that are usually found at the outermost positions of the oligosaccharide chains that are attached to glycoproteins and glycolipids. One of the major types of sialic acids is N-acetylneuraminic acid (NeuSAc), which is the biosynthetic precursor for most of the other types. The substrate molecule can be, as nonlimiting examples, an oligosaccharide, a polysaccharide, a glycoprotein, a ganglioside, or a synthetic molecule. For example, a sialidase can cleave bonds having alpha (2,3)-Gal, alpha (2,6)-Gal, or alpha (2,8)-Gal linkages between a sialic acid residue and the remainder of a substrate molecule. A sialidase can also cleave any or all of the linkages between the sialic acid residue and the remainder of the substrate molecule. Two major linkages between NeuSAc and the penultimate galactose residues of carbohydrate side chains are found in nature, NeuSAc alpha (2,3)-Gal and NeuSAc alpha (2,6)-Gal. Both NeuSAc alpha (2,3)-Gal and NeuSAc alpha (2,6)-Gal molecules can be recognized by influenza viruses as the receptor, although human viruses seem to prefer NeuSAc alpha (2,6)-Gal, avian and equine viruses predominantly recognize NeuSAc alpha (2,3)Gal. A sialidase can be a naturally-occurring sialidase, an engineered sialidase (such as, but not limited to a sialidase whose amino acid sequence is based on the sequence of a naturally-occurring sialidase, including a sequence that is substantially homologous to the sequence of a naturally-occurring sialidase). As used herein, "sialidase" can also mean the active portion of a naturally-occurring sialidase, or a peptide or protein that comprises sequences based on the active portion of a naturally-occurring sialidase.

A "fusion protein" is a protein comprising amino acid sequences from at least two different sources. A fusion protein can comprise amino acid sequence that is derived from a naturally occurring protein or is substantially homologous to all or a portion of a naturally occurring protein, and in addition can comprise from one to a very large number of amino acids that are derived from or substantially homologous to all or a portion of a different naturally occurring protein. In the alternative, a fusion protein can comprise amino acid sequence that is derived from a naturally occurring protein or is substantially homologous to all or a portion of a naturally occurring protein, and in addition can comprise from one to a very large number of amino acids that are synthetic sequences.

A "sialidase catalytic domain protein" is a protein that comprises the catalytic domain of a sialidase, or an amino acid sequence that is substantially homologous to the catalytic domain of a sialidase, but does not comprises the entire amino acid sequence of the sialidase the catalytic domain is derived from, wherein the sialidase catalytic domain protein retains substantially the same activity as the intact sialidase the catalytic domain is derived from. A sialidase catalytic domain protein can comprise amino acid sequences that are not derived from a sialidase, but this is not required. A sialidase catalytic domain protein can comprise amino acid sequences that are derived from or substantially homologous to amino acid sequences of one or more other known proteins, or can comprise one or more amino acids that are not derived from or substantially homologous to amino acid sequences of other known proteins.

I. Composition for Preventing or Treating Infection by a Pathogen

The present disclosure relates to compounds (agents) that include a peptide. The compounds include all or a catalytic portion of a sialidase. In some cases the compound includes at least one domain that can associate the sialidase or portion thereof with a eukaryotic cell. By "peptide or protein-based" compounds, it is meant that a compound that includes a portion having an amino acid framework, in which the amino acids are joined by peptide bonds. A peptide or protein-based compound can also have other chemical compounds or groups attached to the amino acid framework or backbone, including moieties that contribute to the anchoring activity of the anchoring domain, or moieties that contribute to the infection-preventing activity or the sialidase domain. For example, the protein-based therapeutics of the present disclosure can comprise compounds and molecules such as but not limited to: carbohydrates, fatty acids, lipids, steroids, nucleotides, nucleotide analogues, nucleic acid molecules, nucleic acid analogues, peptide nucleic acid molecules, small organic molecules, or even polymers. The protein-based therapeutics of the present disclosure can also comprise modified or non-naturally occurring amino acids. Non-amino acid portions of the compounds can serve any purpose, including but not limited to: facilitating the purification of the compound, improving the solubility or distribution or the compound (such as in a therapeutic formulation), linking domains of the compound or linking chemical moieties to the compound, contributing to the two dimensional or three-dimensional structure of the compound, increasing the overall size of the compound, increasing the stability of the compound, and contributing to the anchoring activity or therapeutic activity of the compound.

The peptide or protein-based compounds of the present disclosure can also include protein or peptide sequences in addition to those that comprise anchoring domains or sialidase domains. The additional protein sequences can serve any purpose, including but not limited to any of the purposes outlined above (facilitating the purification of the compound, improving the solubility or distribution or the compound, linking domains of the compound or linking chemical moieties to the compound, contributing to the two-dimensional or three-dimensional structure of the compound, increasing the overall size of the compound, increasing the stability of the compound, or contributing to the anchoring activity or therapeutic activity of the compound). Preferably any additional protein or amino acid sequences are part of a single polypeptide or protein chain that includes the sialidase domain or domains, but any feasible arrangement of protein sequences is within the scope of the present disclosure.

The anchoring domain and sialidase domain can be arranged in any appropriate way that allows the compound to bind at or near a target cell membrane such that the therapeutic sialidase can exhibit an extracellular activity that prevents or impedes infection of the target cell by a pathogen. The compound will preferably have at least one protein or peptide-based anchoring domain and at least one peptide or protein-based sialidase domain. In this case, the domains can be arranged linearly along the peptide backbone in any order. The anchoring domain can be N-terminal to the sialidase domain, or can be C-terminal to the sialidase domain.

It is also possible to have one or more sialidase domains flanked by at least one anchoring domain on each end. Alternatively, one or more anchoring domains can be flanked by at least one sialidase domain on each end. Chemical, or preferably, peptide, linkers can optionally be used to join some or all of the domains of a compound. It is also possible to have the domains in a nonlinear, branched arrangement. For example, the sialidase domain can be attached to a derivatized side chain of an amino acid that is part of a polypeptide chain that also includes, or is linked to, the anchoring domain.

A compound of the present disclosure can have more than one anchoring domain. In cases in which a compound has more than one anchoring domain, the anchoring domains can be the same or different. A compound of the present disclosure can have more than one sialidase domain. In cases in which a compound has more than one sialidase domain, the sialidase domains can be the same or different. Where a compound comprises multiple anchoring domains, the anchoring domains can be arranged in tandem (with or without linkers) or on alternate sides of other domains, such as sialidase domains. Where a compound comprises multiple sialidase domains, the sialidase domains can be arranged in tandem (with or without linkers) or on alternate sides of other domains, such as, but not limited to, anchoring domains.

A peptide or protein-based compound of the present disclosure can be made by any appropriate way, including purifying naturally occurring proteins, optionally proteolytically cleaving the proteins to obtain the desired functional domains, and conjugating the functional domains to other functional domains. Peptides can also be chemically synthesized, and optionally chemically conjugated to other peptides or chemical moieties. Preferably, however, a peptide or protein-based compound of the present disclosure is made by engineering a nucleic acid construct to encode at least one anchoring domain and at least one sialidase domain together (with or without nucleic acid linkers) in a continuous polypeptide. The nucleic acid constructs, preferably having appropriate expression sequences, can be transfected into prokaryotic or eukaryotic cells, and the therapeutic protein-based compound can be expressed by the cells and purified. Any desired chemical moieties can optionally be conjugated to the peptide or protein-based compound after purification. In some cases, cell lines can be chosen for expressing the protein-based therapeutic for their ability to perform desirable post-translational modifications (such as, but not limited to glycosylation).

A great variety of constructs can be designed and their protein products tested for desirable activities (such as, for example, binding activity of an anchoring domain or catalytic activity of a sialidase domain). The protein products of nucleic acid constructs can also be tested for their efficacy in preventing or impeding infection of a target cell by a pathogen. In vitro and in vivo tests for the infectivity of pathogens are known in the art.

Anchoring Domain

As used herein, an "extracellular anchoring domain" or "anchoring domain" is any moiety that interact with an entity that is at or on the exterior surface of a target cell or is in close proximity to the exterior surface of a target cell. An anchoring domain serves to retain a compound of the present disclosure at or near the external surface of a target cell. An extracellular anchoring domain preferably binds 1) a molecule expressed on the surface of a target cell, or a moiety, domain, or epitope of a molecule expressed on the surface of a target cell, 2) a chemical entity attached to a molecule expressed on the surface of a target cell, or 3) a molecule of the extracellular matrix surrounding a target cell.

An anchoring domain is preferably a peptide or protein domain (including a modified or derivatized peptide or protein domain), or comprises a moiety coupled to a peptide or protein. A moiety coupled to a peptide or protein can be any type of molecule that can contribute to the interaction of the anchoring domain to an entity at or near the target cell surface, and is preferably an organic molecule, such as, for example, nucleic acid, peptide nucleic acid, nucleic acid analogue, nucleotide, nucleotide analogue, small organic molecule, polymer, lipids, steroid, fatty acid, carbohydrate, or any combination of any of these.

Target tissue or target cell type includes the sites in an animal or human body where a pathogen invades or amplifies. For example, a target cell can be a lung cell that can be infected by EV-D68. A compound or agents of the present disclosure can comprise an anchoring domain that can interact with a cell surface entity, for example, that is specific for the target cell type.

A compound for treating infection by a pathogen can comprise an anchoring domain that can bind at or near the surface of a target cell. For example, heparin/sulfate, closely related to heparin, is a type of GAG that is ubiquitously present on cell membranes, including the surface of respiratory epithelium. Many proteins specifically bind to heparin/heparan sulfate, and the GAG-binding sequences in these proteins have been identified (Meyer, F A, King, M and Gelman, R A. (1975) *Biochimica et BiophysicaActa* 392: 223-232; Schauer, S. ed., pp 233. Sialic Acids Chemistry, Metabolism and Function. Springer-Verlag, 1982). For example, the GAG-binding sequences of human platelet factor 4 (PF4) (SEQ ID NO:2), human interleukin 8 (IL8) (SEQ ID NO:3), humanantithrombin III (AT III) (SEQ ID NO:4), human apoprotein E (ApoE) (SEQ ID NO:5), human angio-associated migratory cell protein (AAMP) (SEQ ID NO:6), or human amphiregulin (SEQ ID NO:7) have been shown to have very high affinity (in the nanomolar range) towards heparin (Lee, M K and Lander, A D. (1991) Pro Natl Acad Sci USA 88:2768-2772; Goger, B, Halden, Y, Rek, A, Mosl, R, Pye, D. Gallagher, J and Kungl, A J. (2002) Biochem. 41:1640-1646; Witt, D P and Lander AD (1994) Curr Bio 4:394-400; Weisgraber, K H, Rail, S C, Mahley, R W, Milne, R W and Marcel, Y. (1986) J Bio Chem 261: 2068-2076). These sequences, or other sequences that have been identified or are identified in the future as heparin/heparan sulfate binding sequences, or sequences substantially homologous to identified heparin/heparan sulfate binding sequences that have heparin/heparan sulfate binding activity, can be used as epithelium-anchoring-domains in compounds of the present disclosure that can be used.

Sialidase Domain

A sialidase that can cleave more than one type of linkage between a sialic acid residue and the remainder of a substrate molecule, in particular, a sialidase that can cleave both α(2, 6)-Gal and α(2, 3)-Gal linkages can be used in the compounds of the disclosure. Sialidases include are the large bacterial sialidases that can degrade the receptor sialic acids Neu5Ac alpha(2,6)-Gal and Neu5Ac alpha(2,3)-Gal. For example, the bacterial sialidase enzymes from *Clostridium perfringens* (Genbank Accession Number X87369), *Actinomyces viscosus, Arthrobacter ureafaciens*, or *Micromonospora viridifaciens* (Genbank Accession Number D01045) can be used. Sialidase domains of compounds of the present disclosure can comprise all or a portion of the amino acid sequence of a large bacterial sialidase or can comprise amino acid sequences that are substantially homologous to all or a portion of the amino acid sequence of a large bacterial sialidase. In one preferred embodiment, a sialidase domain comprises a sialidase encoded by *Actinomyces viscosus*, such as that of SEQ ID NO: 12, or such as sialidase sequence substantially homologous to SEQ ID NO: 12. In yet another preferred embodiment, a sialidase domain comprises the catalytic domain of the *Actinomyces viscosus* sialidase extending from amino acids 274-666 of SEQ ID NO:12, or a substantially homologous sequence.

Additional sialidases include the human sialidases such as those encoded by the genes NEU2 (SEQ ID NO:8; Genbank Accession Number Y16535; Monti, E, Preti, Rossi, E., Ballabio, A and Borsani G. (1999) *Genomics* 57:137-143) and NEU4 (SEQ ID NO:9; Genbank Accession Number NM080741; Monti et al. (2002) *Neurochem Res* 27:646-663). Sialidase domains of compounds of the present disclosure can comprise all or a portion of the amino acid sequences of a sialidase or can comprise amino acid sequences that are substantially homologous to all or a portion of the amino acid sequences of a sialidase. Preferably, where a sialidase domain comprises a portion of the amino acid sequences of a naturally occurring sialidase, or sequences substantially homologous to a portion of the amino acid sequences of a naturally occurring sialidase, the portion comprises essentially the same activity as the intact sialidase. The present disclosure also includes sialidase catalytic domain proteins. As used herein a "sialidase catalytic domain protein" comprises a catalytic domain of a sialidase but does not comprise the entire amino acid sequence of the sialidase from which the catalytic domain is derived. A sialidase catalytic domain protein has sialidase activity. Preferably, a sialidase catalytic domain protein comprises at least 10%, at least 20%, at least 50%, at least 70% of the activity of the sialidase from which the catalytic domain sequence is derived. More preferably, a sialidase catalytic domain protein comprises at least 90% of the activity of the sialidase from which the catalytic domain sequence is derived.

A sialidase catalytic domain protein can include other amino acid sequences, such as but not limited to additional sialidase sequences, sequences derived from other proteins, or sequences that are not derived from sequences of naturally occurring proteins. Additional amino acid sequences can perform any of a number of functions, including contributing other activities to the catalytic domain protein, enhancing the expression, processing, folding, or stability of the sialidase catalytic domain protein, or even providing a desirable size or spacing of the protein.

A preferred sialidase catalytic domain protein is a protein that comprises the catalytic domain of the *A. viscosus* sialidase. Preferably, an *A. viscosus* sialidase catalytic domain protein comprises amino acids 270-666 of the *A. viscosus* sialidase sequence (SEQ ID NO:12). Preferably, an *A. viscosus* sialidase catalytic domain protein comprises an amino acid sequence that begins at any of the amino acids from amino acid 270 to amino acid 290 of the *A. viscosus* sialidase sequence (SEQ ID NO: 12) and ends at any of the amino acids from amino acid 665 to amino acid 901 of said *A. viscosus* sialidase sequence (SEQ ID NO: 12), and lacks any *A. viscosus* sialidase protein sequence extending from amino acid 1 to amino acid 269. (As used herein "lacks any *A. viscosus* sialidase protein sequence extending from amino acid 1 to amino acid 269" means lacks any stretch of four or more consecutive amino acids as they appear in the designated protein or amino acid sequence.)

In some preferred embodiments, an *A. viscosus* sialidase catalytic domain protein comprises amino acids 274-681 of the *A. viscosus* sialidase sequence (SEQ ID NO: 12) and lacks other *A. viscosus* sialidase sequence. In some preferred embodiments, an *A. viscosus* sialidase catalytic domain protein comprises amino acids 274-666 of the *A. viscosus* sialidase sequence (SEQ ID NO: 12) and lacks any other *A. viscosus* sialidase sequence. In some preferred embodiments, an *A. viscosus* sialidase catalytic domain protein comprises amino acids 290-666 of the *A. viscosus* sialidase sequence (SEQ ID NO: 12) and lacks any other *A. viscosus* sialidase sequence. In yet other preferred embodiments, an *A. viscosus* sialidase catalytic domain protein comprises amino acids 290-681 of the *A. viscosus* sialidase sequence (SEQ ID NO: 12) and lacks any other *A. viscosus* sialidase sequence.

Linkers

A compound of the present disclosure can optionally include one or more linkers that can join domains of the compound. Linkers can be used to provide optimal spacing or folding of the domains of a compound. The domains of a compound joined by linkers can be sialidase domains, anchoring domains, or any other domains or moieties of the compound that provide additional functions such as enhancing compound stability, facilitating purification, etc. A linker used to join domains of compounds of the present disclosure can be a chemical linker or an amino acid or peptide linker. Where a compound comprises more than one linker, the linkers can be the same or different. Where a compound comprises more than one linker, the linkers can be of the same or different lengths.

Many chemical linkers of various compositions, polarity, reactivity, length, flexibility, and cleavability are known in the art of organic chemistry. Preferred linkers of the present disclosure include amino acid or peptide linkers. Peptide linkers are well known in the art. Preferably linkers are between one and one hundred amino acids in length, and more preferably between one and thirty amino acids in length, although length is not a limitation in the linkers of the compounds of the present disclosure. Preferably linkers comprise amino acid sequences that do not interfere with the conformation and activity of peptides or proteins encoded by monomers of the present disclosure. Some preferred linkers of the present disclosure are those that include the amino acid glycine. For example, linkers having the sequence: (GGGGS (SEQ ID NO:10))n, where n is a whole number between I and 20, or more preferably between I and 12, can be used to link domains of therapeutic compounds of the present disclosure.

The present disclosure also includes nucleic acid molecules that encode protein-based compounds of the present disclosure that comprise at least one sialidase domain and at least one anchoring domain. The nucleic acid molecules can have codons optimized for expression in particular cell types, such as, for example *E. coli* or human cells. The nucleic acid molecules or the present disclosure that encode protein-based compounds of the present disclosure that comprise at least one sialidase domain and at least one anchoring domain can also comprise other nucleic acid sequences, including but not limited to sequences that enhance gene expression. The nucleic acid molecules can be in vectors, such as but not limited to expression vectors.

Administration

The compound is administered so that it comes into contact with the target cells, but is preferably not administered systemically to the patient. Thus, in the case of infection of the lung, a composition comprising a sialidase (e.g., a composition comprising DAS181 (e.g., SEQ ID NO:15 or 16) can be administered by inhalation.

II. Pharmaceutical Compositions

The present disclosure includes compounds of the present disclosure formulated as pharmaceutical compositions. The pharmaceutical compositions comprise a pharmaceutically acceptable carrier prepared for storage and preferably subsequent administration, which have a pharmaceutically effective amount of the compound in a pharmaceutically acceptable carrier or diluent. Acceptable carriers or diluents for therapeutic use are well known in the pharmaceutical art, and are described, for example, in Remington's Pharmaceutical Sciences, 18th Ed., Mack Publishing Co., Easton, Pa. (1990)). Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

The pharmaceutically effective amount of a test compound required as a dose will depend on the route of administration, the type of animal or patient being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the present disclosure, the pharmaceutical compositions can be used alone or in combination with one another, or in combination with other therapeutic or diagnostic agents. These products can be utilized in vivo, preferably in a mammalian patient, preferably in a human, or in vitro. In employing them in vivo, the pharmaceutical compositions can be administered to the patient in a variety of ways, preferably topically to the target cells, topically to the locus of infection or topically to tissue comprising the target cells.

Accordingly, in some embodiments, the methods comprise administration of the agent and a pharmaceutically acceptable carrier. In some embodiments, the ophthalmic composition is a liquid composition, semi-solid composition, insert, film, microparticles or nanoparticles.

III. Method of Treating an Infection by a Pathogen

The method of the present disclosure includes: treating a subject that is infected with EV-D68 or at risk of being infected with EV-D68 with a pharmaceutical composition of the present disclosure that comprises a protein-based compound that comprises a sialidase activity. In some preferred embodiments the method includes applying a therapeutically effective amount of a pharmaceutical composition of the present disclosure to target cells of a subject. The sialidase activity can be an isolated naturally occurring sialidase protein, or a recombinant protein substantially homologous to at least a portion of a naturally occurring sialidase. A preferred pharmaceutical composition comprises a sialidase with substantial homology to the *A. viscosus* sialidase (SEQ ID NO:12). The subject to be treated can be an animal or human subject. In yet another aspect, the method includes: treating a subject that is infected with EV-D68 with a pharmaceutical composition of the present disclosure that comprises a protein-based compound that comprises a sialidase catalytic domain (e.g., SEQ ID: 15 or SEQ ID NO:16 or a polypeptide comprising amino acids 274-666 of the *A. viscosus* sialidase sequence (SEQ ID NO: 12) and lacks any other *A. viscosus* sialidase sequence). In some preferred embodiments, the method includes applying a therapeutically effective amount of a pharmaceutical composition of the present disclosure to epithelial cells of a subject. The sialidase catalytic domain is preferably substantially homologous to the catalytic domain of a naturally occurring sialidase. A preferred pharmaceutical composition comprises a sialidase catalytic domain with substantial homology to amino acids 274-666 the *A. viscosus* sialidase (SEQ ID NO: 12). The subject to be treated can be an animal or human subject. In some cases the compound is DAS181 (SEQ ID NO: 15 or 16).

Dosage

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. In non-human animal studies, applications of the pharmaceutical compositions are commenced at higher dose levels, with the dosage being decreased until the desired effect is no longer achieved or adverse side effects are reduced or disappear. The dosage for a compound of the present disclosure can range broadly depending upon the desired affects, the therapeutic indication, route of administration and purity and activity of the compound. Typically, human clinical applications of products are commenced at lower dosage levels, with dosage level being increased until the desired effect is achieved. Alternatively, acceptable in vitro studies can be used to establish useful doses and routes of administration of the test compound. Typically, dosages can be between about 1 ng/kg and about 10 mg/kg, preferably between about 10 ng/kg and about 1 mg/kg, and more preferably between about 100 ng/kg and about 100 micrograms/kg.

In one preferred regimen, appropriate dosages are administered to each patient by either eyedrop, spray, or by aerosol. It will be understood, however, that the specific dose level and frequency of dosage for any particular patient may be varied and will depend upon a variety of factors including the activity of the specific salt or other form employed, the metabolic stability and length of action of that compound, the age of the patient, body weight of the patient, general health of the patient, sex of the patient, diet of the patient, mode and time of administration, rate of excretion, drug combination, the severity of the particular condition, and the host undergoing therapy.

EXAMPLES

Example 1: Preparation of DAS181

DAS181 is a fusion protein containing the heparin (glysosaminoglycan, or GAG) binding domain from human amphiregulin fused via its N-terminus to the C-terminus of a catalytic domain of *Actinomyces Viscosus* (e.g., sequence of amino acids set forth in SEQ ID NO: 13 (no amino terminal methionine) and SEQ ID NO: 14 (including amino terminal methionine). The DAS181 protein used in the examples below was purified as described in Malakhov et al., *Antimicrob. Agents Chemother.*, 1470-1479 (2006), which is incorporated in its entirety by reference herein. Briefly, the DNA fragment coding for DAS181 was cloned into the plasmid vector pTrc99a (Pharmacia) under the control of an IPTG (isopropyl-ß-D-thiogalactopyranoside)-inducible promoter. The resulting construct was expressed in the BL21 strain of *Escherichia Coli* (*E. coli*). The *E. coli* cells expressing the DAS181 protein were washed by diafiltration in a fermentation harvest wash step using Toyopcarl buffer 1, UFP-500-E55 hollow fiber cartridge (GE Healthcare) and a Watson-Marlow peristaltic pump. The recombinant DAS181 protein was then purified in bulk from the cells as described in US 20050004020 and US 20080075708, which are incorporated in their entirety by reference herein.

The sialidase activity of DAS181 was measured using the fluorogenic substrate 4-methylumbelliferyl-N-acetyl-α-D-neuraminic acid (4-MU-NANA; Sigma). One unit of sialidase is defined as the amount of enzyme that releases 10 nmol of MU from 4-MU-NANA in 10 minutes at 37° C. (50 mM $CH_3COOH$—NaOH buffer, pH 5.5) in a reaction that contains 20 nmol of 4-MU-NANA in a 0.2 ml volume (Potier et al., *Anal. Biochem.*, 94:287-296, 1979). The specific activity of DAS181 was determined to be 1,300 U/mg protein (0.77 µg DAS181 protein per unit of activity).

Example 2: Testing of DAS181 and Additional Agents for Activity Against EV-D68

Various potential potential therapeutic agents for treatment of EV-D68 disease were tested in a cell culture assay.

Among the agents tested were agents developed specifically for RV or EV indications, drugs that inhibit influenza virus, and several drugs that are FDA-approved for other indications. The 46 compounds tested included picornavirus capsid inhibitors pleconaril (Thibaut et al. 2012. Combating enterovirus replication: State-of-the-art on antiviral research. *Biochem Pharmacol* 83:185-192), pocapavir (V-073; ViroDefense, Washington, D.C.) (Oberste et al. 2009. In vitro antiviral activity of V-073 against polioviruses. *Antimicrob Agents Chemother* 53:4501-4503), and vapendavir (BTA-798; Biota Holdings, Alpharetta, Ga.) (Thibaut et al. 2012. Combating enterovirus replication: State-of-the-art on antiviral research. *Biochem Pharmacol* 83:185-192); the enterovirus 2C inhibitor KR-22865 (Korea Research Institute for Chemical Technology, Seoul, Republic of Korea); picornavirus protease inhibitors rupintrivir (AG-7088; Pfizer, Groton, Conn.) (Binford et al. 2005. Conservation of amino acids in human rhinovirus 3C protease correlates with broad-spectrum antiviral activity of rupintrivir, a novel human rhinovirus 3C protease inhibitor. *Antimicrob Agents Chemother* 49:619-626) and V-7404 (ViroDefense) (Rhoden et al. 2013. Anti-poliovirus activity of protease inhibitor AG-7404, and assessment of in vitro activity in combination with antiviral capsid inhibitor compounds. *Antiviral Res* 98:186-191); and the viral polymerase inhibitor favipiravir (T-705; Toyama Chemical Co., Toyama, Japan) (Furuta et al. 2002. In vitro and in vivo activities of anti-influenza virus compound T-705. *Antimicrob Agents Chemother* 46:977-981). DAS181 is an inhibitor of influenza virus binding to α2,6-linked sialic acids (Ansun Biopharma, San Diego, Calif.) (Moss et al. 2012. A phase II study of DAS181, a novel host directed antiviral for the treatment of influenza infection. *J Infect Dis* 206:1844-1851). In addition to these antiviral compounds, agents that were originally developed and approved for other indications but have been shown subsequently to have antiviral activity against one or more EV or RV. These include fluoxetine (selective serotonin reuptake inhibitor anti-depressant) (Ulferts et al. 2013. Selective serotonin reuptake inhibitor fluoxetine inhibits replication of human enteroviruses B and D by targeting viral protein 2C. *Antimicrob Agents Chemother* 57:1952-1956), formoterol (bronchodilator) (Bochkov et al. 2013. Budesonide and formoterol effects on rhinovirus replication and epithelial cell cytokine responses. *Respir Res* 14:98), and itraconazole (antifungal) (Strating et al. 2015. Itraconazole Inhibits Enterovirus Replication by Targeting the Oxysterol-Binding Protein. *Cell Reports* 10:600-615). Two additional drugs, mefloquine (anti-malarial) and nitazoxanide (anti-protozoal) have also been reported to have activity against several virus families, though not necessarily picornaviruses (Brickelmaier et al. 2009. Identification and characterization of mefloquine efficacy against JC virus in vitro. *Antimicrob Agents Chemother* 53:1840-1849; Rossignol. 2014. Nitazoxanide: a first-in-class broad-spectrum antiviral agent. *Antiviral Res* 110:94-103). These five drugs were purchased from Sigma. Aldrich, St. Louis, Mo.

Antiviral activity was assessed in a homogeneous cell-based assay that measured inhibition of viral cytopathic effect in human rhabdomyosdarcoma cells (RD; ATCC CCL-136). The viruses included three representative EV-D68 strains from the 2014 outbreak (USA-MO/18947, USA-MO/18949, USA-IL/18956) (Brown et al. 2014. Seven Strains of Enterovirus D68 Detected in the United States during the 2014 Severe Respiratory Disease Outbreak. *Genuine Announce* 2:e01201-01214), as well as the 1962 prototype strain (Fermon) (Schieble et al. 1967. A probable new human picornavirus associated with respiratory diseases. *Am J Epidemiol* 85:297-310). For the CPE inhibition assay, half-$\log_{10}$ dilutions of drug compound (10 μM to 0.001 μM) were combined with 100 $CCID_{50}$ (50% cell culture infectious dose) of virus and added to monolayers of RD cells (5000 cells per well) in 384-well, white, flat-bottom microplates. Plates were incubated at 33° C. and 5% $CO_2$ for five days, and cell viability was assessed using ATPLite® (Perkin Elmer, Waltham, Mass.) by adding 15 μL of cell lysis buffer and then 15 μL of substrate solution, following the manufacturer's recommendations. Luminescence was read in a plate reader and the 50% effective concentration ($EC_{50}$) of each compound was calculated by 4-parameter curve-fitting with GraphPad Prism® (version 5.0.3; GraphPad Software, La Jolla, Calif.). The results of this analysis are shown in Table 1.

TABLE 1

Efficacy of various agents against four EV-D68 Strains

| | Mean $EC_{50}$ ± SD (μM) | | | |
|---|---|---|---|---|
| | USA-MO/18947 | USA-MO/18949 | USA-IL/18956 | Fermon |
| EV/RV Capsid inhibitors | | | | |
| Pleconaril[a,b] | 4.44 ± 0.55 | 6.09 ± 0.26 | 6.11 ± 1.05 | 0.38 ± 0.01 |
| Pocapavir[a] | >10 | >10 | >10 | >10 |
| Vapendavir[a] | >10 | >10 | >10 | >10 |
| EV/RV 2C inhibitor | | | | |
| KR-22865 | 0.0028 ± 0.0006 | 0.0037 ± 0.001 | 0.0051 ± 0.0013 | 0.003 ± 0.001 |
| EV/RV Protease inhibitors | | | | |
| Rupintrivir[a] | 0.0046 ± 0.0016 | 0.0015 ± 0.003 | 0.0037 ± 0.007 | 0.002 ± 0.0005 |
| V-7404[c] | 0.026 ± 0.004 | 0.027 ± 0.008 | 0.024 ± 0.007 | 0.0035 ± 0.0006 |
| Influenza inhibitors | | | | |
| Amantidine[d] | >10 | >10 | >10 | >10 |
| Arbidol[a,e] | >10 | >10 | >10 | >10 |
| DAS181[a] | 0.0036 ± 0.0015 | 0.0026 ± 0.0012 | 0.004 ± 0.0016 | 0.0012 ± 0.0009 |
| Favipiravir[a] | >10 | >10 | >10 | >10 |
| Oseltamivir[d] | >10 | >10 | >10 | >10 |

TABLE 1-continued

Efficacy of various agents against four EV-D68 Strains

|  | Mean $EC_{50}$ ± SD (μM) | | | |
| --- | --- | --- | --- | --- |
|  | USA-MO/18947 | USA-MO/18949 | USA-IL/18956 | Fermon |
| Approved for other indications | | | | |
| Fluoxetine[d] | 0.53 ± 0.15 | 0.64 ± 0.17 | 1.05 ± 0.2 | 0.34 ± 0.04 |
| Formoterol fumarate[d] | >10 | >10 | >10 | >10 |
| Itraconazole[d] | >10 | >10 | >10 | >10 |
| Mefloquine[d] | >10 | >10 | >10 | >10 |
| Nitazoxanide[d] | >10 | >10 | >10 | >10 |

[a]Completed a Phase II clinical trial but not yet FDA-approved.
[b]In HeLa H1 cells, the EC50 values for the four strains were 0.131 ± 0.024, 0.358 ± 0.036, 0.321 ± 0.094, 0.36 ± 0.021, respectively, for pleconaril. For other compounds, the values were not significantly different in the two cell lines (data not shown).
[c]Completed a Phase I clinical safety trial.
[d]FDA-approved for an indication other than EV/RV infection
[e]Licensed for human use in Russia and China.

Pleconaril inhibited the Fermon strain with an $EC_{50}$ value of 0.38±0.01 μM but activity against the 2014 strains was detected only at concentrations greater than 4 μM (Table 1). Two other capsid inhibitors, pocapavir and vapendavir, were inactive against all four EV-D68 strains. KR-22865, rupintrivir, and V-7404 were highly active against all four EV-D68 strains, with $EC_{50}$ values of 0.0015-0.0051 μM (Table 1). Of five influenza inhibitors tested, only DAS181 inhibited EV-D68, with $EC_{50}$ values comparable to those of the 2C and protease inhibitors (0.0012-0.004 μM; Table 1). Fluoxetine (Prozac®; a selective serotonin reuptake inhibitor) inhibited the EV-D68 strains at concentrations of 0.34-1.05 μM (Table 1). Four other compounds that have been reported to have antiviral activity had no activity against the EV78 D68 strains, even at the highest concentration tested (10 μM) (Table 1).

Fourteen of the 16 compounds tested have completed at least Phase II clinical trials and seven are already FDA-approved for other indications. Fluoxetine was the only FDA-approved drug that had significant activity against EV-D68. However, fluoxetine's psychoactive properties, and its intended use to treat depression and other psychological disorders, suggest that the potential risk of unintended effects may outweigh the benefit of using it to treat EV-D68 infection. Furthermore, given typical fluoxetine dosing and maximal plasma levels (<200 nM), it is unlikely that virus inhibitory concentrations can be achieved in vivo.

In our hands, itraconazole failed to inhibit any EV-D68 strain in our standard assay at any concentration tested (Table 1), contrary to two published reports that determined $EC_{50}$ values of 0.32 μM to 0.43 μM for the Fermon strain (Gao et al. 2015. Discovery of itraconazole with broad-spectrum in vitro antienterovirus activity that targets non-structural protein 3A. *Antimicrob Agents Chemother* 59:2654-2665; Strating et al. 2015. Itraconazole inhibits enterovirus replication by targeting the oxysterol-binding protein. *Cell Reports* 10:600-615). In both studies, the methods were somewhat different from our approach. Gao et al. (Gao et al. 2015. Discovery of itraconazole with broad-spectrum in vitro antienterovirus activity that targets non-structural protein 3A. *Antimicrob Agents Chemother* 59:2654-2665) used virus titer as their readout and observed a titer reduction of only 1.5 log, to $10^5$ $CCID_{50}$/ml, even at drug concentrations >1 μM. The study reported in Strating et al. (Strating et al. 2015. Itraconazole inhibits enterovirus replication by targeting the oxysterol-binding protein. Cell reports 10:600-615) infected with "the lowest MOI that resulted in full CPE within 3 days" and used a CPE reduction assay similar to ours. Itraconazole activity appears to be very sensitive to virus dose, such that very different $EC_{50}$ values (0.29 μM to >10 μM for the Fermon strain) are obtained within a relatively narrow range of virus doses (100-fold dose range, using five half-log dilutions; data not shown). For the other compounds tested, similar $EC_{50}$ values were observed across this same dose range. For pleconaril, for example, the $EC_{50}$ varied only from 0.3 μM to 0.5 μM. We believe our assay represents a more stringent test of activity and is more likely to predict clinical relevance of the compounds tested. Pleconaril was originally developed for treatment of EV and RV infections and it has broad activity against a wide range of RV and EV serotypes (Pevear et al. 1999. Activity of pleconaril against enteroviruses. *Antimicrob Agents Chemother* 43:2109-2115). In RD cells, the activity of pleconaril against the Feimon strain was similar to that recently reported by Liu et al. (Liu et al. 2015. Structure and inhibition of EV-D68, a virus that causes respiratory illness in children. *Science* 347:71-74); however, its $EC_{50}$ value was about 10-fold higher against the 2014 strains (Table 1). Upon repeat testing in the HeLa H1 cells used by Liu et al., we obtained EC50 values of 0.13-0.36 μM for all four strains (Table 1), suggesting a cell specific difference in drug susceptibility. Interestingly, the $EC_{50}$ values for the other compounds were similar in both cell lines; the nature of the difference in pleconaril susceptibility remains unknown but is under investigation.

The four most promising compounds strongly inhibited all four EV-D68 strains tested, at low nanomolar concentrations (Table 1). Two of these are in active development for other viral infections; rupintrivir and KR-22865 are not currently being developed further. V-7404 is being developed in combination with pocapavir for treatment of poliovirus infections, especially in immunodeficient persons who are chronically infected and at risk for paralysis, in support of the global polio eradication endgame strategy (Collett et al. 2008. A case for developing antiviral drugs against polio. *Antiviral Res* 79:179-187; De Palma et al. 2008. Potential use of antiviral agents in polio eradication. *Emerg Infect Dis* 14:545-551). DAS181 is a sialidase that cleaves α2,6-linked sialic acids on the surface of cells, thus inhibiting binding of neuraminidase, is being developed to treat influenza and parainfluenza infections (Belser et al. 2007. DAS181, a novel sialidase fusion protein, protects mice from lethal avian influenza H5N1 virus infection. *J Infect Dis* 196:1493-1499).

Example 3: Preparation of DAS181 Microparticles

The following process is used to prepate DAS181 microparticles suitable for use in inhalation therapy,
  (a) 75 mg/ml Histidine, 0.107M citric acid, pH 5.0 and 1M Trehalose stock solutions were sterile filtered into and combined in an Excipient Bottle.
  (b) The contents of the Excipient Bottle were added, with mixing, to a Compounding Vessel containing 125 mg/ml DAS181 protein prepared as described in Example 1.
  (c) Isopropanol was sterile filtered into an Isopropanol Bag
  (d) The content of the Isopropanol Bag was pumped into the Compounding Vessel while mixing vigorously to form the Feedstock Solution. The final composition of the Feedstock Solution was as follows: 70 mg/ml DAS181, 26% isopropanol, 9.8 mg/ml histidine, 9.8 mg/ml trehalose, 2.69 mg/ml citric acid, pH 5.0. The time between initiating the addition of isopropanol and starting the lyophilization cycle was between 90 minutes and 120 minutes
  (e) Stainless Steel trays that had undergone depyrogenation were each filled with 950 g of the Feedstock Solution, using a metering pump
  (f) The filled Stainless Steel trays were subjected to a Lyophilization Cycle as follows:
    a. the feedstock solution in the lyophilization trays were gasketed and placed in the lyophilizer shelves at 25° C. for 5 minutes;
    b. the temperature of the shelves was lowered to −55° C. at a ramp rate of −0.4° C. minute;
    c. the trays were held at −55° C. for between 60 and 180 minutes;
    d. primary drying was accomplished by setting the condenser to <−60° C., applying a vacuum of 125 mTorr with 250 mTorr dead band and increasing the temperature to −40° C. at a ramp rate of 0.125° C./minute and further to a temperature of −30° C. at 0.167° C./minute;
    e. the temperature was held at −30° C. for between 5000 and 6500 minutes;
    f. secondary drying was accomplished by increasing the temperature to 15° C. at a ramp rate of 0.5° C./minute, holding at 15° C. for 30 minutes, then further ramping up to a temperature of 30° C. at a ramp rate of 0.5/minute;
    g. the temperature was held at 30° C. for between 300 and 500 minutes; and
    h. the vacuum was released and the lyophilizer was backfilled with nitrogen to prevent oxidation of the microparticle formulations before transferring into bottles for bulk mixing and aliquoting the bulk powder for storage at ≤−15° C.

The DAS181 dry powder microparticles prepared according to the above method have a mass median aerodynamic diameter (MMAD) of about 10 microns and a GSD of between 1 and 2. Such particles are suitable for use in inhalers for treatment of respiratory infection.

Example 4: DAS181 Testing Against EV-D68 Strains

As shown in the Table 2, DAS181 was tested to assess antiviral activity of the compound using a cell-based assay, and using enterovirus D68 strains (EV-D68). In this assay, using four specific EV-D68 strains, the compound was added at different time-points to each of the strains. The three time conditions tested were: (i) DAS181 preincubated with cells for 24 h before virus infection; (ii) DAS181 added simultaneously with virus; and (iii) DAS181 added 4 h post-infection. Fermon, an original prototypic strain, was used as control. The data demonstrated there was no effect of time of addition on the EC50 of the compound and the compound showed low micromolar potency in all conditions tested, and against all the enterovirus strains tested.

TABLE 2

DAS181 specific anti-viral assay against EV-D68 strains

| Assay Condition | DAS181 Mean EC50 ± SD (µM) | | | |
| --- | --- | --- | --- | --- |
| | USA-MO/238102 | USA-MO/238121 | USA-IL/238139 | Fermon |
| 24 hr preincubation before infection | 0.002 ± 0.0001 | 0.0027 ± 0.0004 | 0.0032 ± 0.001 | 0.001 ± 0.0001 |
| No preincubation | 0.0036 ± 0.0015 | 0.0026 ± 0.0012 | 0.004 ± 0.0016 | 0.0012 ± 0.0009 |
| Drug addition 4 hr after infection | 0.0043 ± 0.0004 | 0.0034 ± 0.001 | 0.004 ± 0.0012 | 0.0036 ± 0.0015 |

The invention claimed is:

1. A method of treating Human enterovirus D68 infection in a patient, the method comprising administering to the patient an effective amount of a liquid composition comprising a polypeptide comprising the amino acid sequence of SEQ ID NO:15, wherein the composition is administered by inhalation.

2. The method of claim 1, wherein the liquid composition is administered to the patient before the patient exhibits a symptom of infection by Human enterovirus D68.

3. The method of claim 1, wherein the patient suffers from asthma.

4. The method of claim 1, wherein the patient immunocompromised.

5. The method of claim 1, wherein the patient is under age 18.

6. The method of claim 1, wherein the patient is under age 10.

7. The method of claim 1, further comprising administering a capsid inhibitor.

8. The method of claim 1, further comprising administering an agent selected from the group consisting of: pleconaril, pocapavir, orvapendavir, vapendavir, KR-22865, rupintrivir, V-7404, amantadine, arbidol, favipiravir, oseltamivir, fluoxetine, formoterol fumarate, itraconazole, mefloquine, and nitazoxanide.

* * * * *

SEQUENCE LISTING

<160> NUMBER OF SEQ ID NOS: 16

<210> SEQ ID NO 1
<211> LENGTH: 58
<212> TYPE: PRT
<213> ORGANISM: Bos taurus

<400> SEQUENCE: 1

Arg Pro Asp Phe Cys Leu Glu Pro Pro Tyr Thr Gly Pro Cys Lys Ala
1               5                   10                  15

Arg Ile Ile Arg Tyr Phe Tyr Asn Ala Lys Ala Gly Leu Cys Gln Thr

```
            20              25              30
Phe Val Tyr Gly Gly Cys Arg Ala Lys Arg Asn Asn Phe Lys Ser Ala
         35              40              45
Glu Asp Cys Met Arg Thr Cys Gly Gly Ala
         50              55
```

<210> SEQ ID NO 2
<211> LENGTH: 24
<212> TYPE: PRT
<213> ORGANISM: Homo sapiens

<400> SEQUENCE: 2

```
Asn Gly Arg Arg Ile Cys Leu Asp Leu Gln Ala Pro Leu Tyr Lys Lys
1               5                   10                  15
Ile Ile Lys Lys Leu Leu Glu Ser
            20
```

<210> SEQ ID NO 3
<211> LENGTH: 27
<212> TYPE: PRT
<213> ORGANISM: Homo sapiens

<400> SEQUENCE: 3

```
Gly Arg Glu Leu Cys Leu Asp Pro Lys Glu Asn Trp Val Gln Arg Val
1               5                   10                  15
Val Glu Lys Phe Leu Lys Arg Ala Glu Asn Ser
            20                  25
```

<210> SEQ ID NO 4
<211> LENGTH: 34
<212> TYPE: PRT
<213> ORGANISM: Homo sapiens

<400> SEQUENCE: 4

```
Gln Ile His Phe Phe Phe Ala Lys Leu Asn Cys Arg Leu Tyr Arg Lys
1               5                   10                  15
Ala Asn Lys Ser Ser Lys Leu Val Ser Ala Asn Arg Leu Phe Gly Asp
            20                  25                  30
Lys Ser
```

<210> SEQ ID NO 5
<211> LENGTH: 34
<212> TYPE: PRT
<213> ORGANISM: Homo sapiens

<400> SEQUENCE: 5

```
Glu Leu Arg Val Arg Leu Ala Ser His Leu Arg Lys Leu Arg Lys Arg
1               5                   10                  15
Leu Leu Arg Asp Ala Asp Asp Leu Gln Lys Arg Leu Ala Val Tyr Gln
            20                  25                  30
Ala Gly
```

<210> SEQ ID NO 6
<211> LENGTH: 12
<212> TYPE: PRT
<213> ORGANISM: Homo sapiens

<400> SEQUENCE: 6

```
Arg Arg Leu Arg Arg Met Glu Ser Glu Ser Glu Ser
1               5                   10
```

<210> SEQ ID NO 7
<211> LENGTH: 21
<212> TYPE: PRT
<213> ORGANISM: Homo sapiens

<400> SEQUENCE: 7

Lys Arg Lys Lys Lys Gly Gly Lys Asn Gly Lys Asn Arg Arg Asn Arg
1               5                   10                  15

Lys Lys Lys Asn Pro
            20

<210> SEQ ID NO 8
<211> LENGTH: 379
<212> TYPE: PRT
<213> ORGANISM: Homo sapiens

<400> SEQUENCE: 8

Met Ala Ser Leu Pro Val Leu Gln Lys Glu Ser Val Phe Gln Ser Gly
1               5                   10                  15

Ala His Ala Tyr Arg Ile Pro Ala Leu Leu Tyr Leu Pro Gly Gln Gln
            20                  25                  30

Ser Leu Leu Ala Phe Ala Glu Gln Arg Ala Ser Lys Lys Asp Glu His
        35                  40                  45

Ala Glu Leu Ile Val Leu Arg Arg Gly Asp Tyr Asp Ala Pro Thr His
50                  55                  60

Gln Val Gln Trp Gln Ala Gln Glu Val Val Ala Gln Ala Arg Leu Asp
65                  70                  75                  80

Gly His Arg Ser Met Asn Pro Cys Pro Leu Tyr Asp Ala Gln Thr Gly
                85                  90                  95

Thr Leu Phe Leu Phe Phe Ile Ala Ile Pro Gly Gln Val Thr Glu Gln
            100                 105                 110

Gln Gln Leu Gln Thr Arg Ala Asn Val Thr Arg Leu Cys Gln Val Thr
        115                 120                 125

Ser Thr Asp His Gly Arg Thr Trp Ser Ser Pro Arg Asp Leu Thr Asp
130                 135                 140

Ala Ala Ile Gly Pro Ala Tyr Arg Glu Trp Ser Thr Phe Ala Val Gly
145                 150                 155                 160

Pro Gly His Cys Leu Gln Leu Asn Asp Arg Ala Arg Ser Leu Val Val
                165                 170                 175

Pro Ala Tyr Ala Tyr Arg Lys Leu His Pro Ile Gln Arg Pro Ile Pro
            180                 185                 190

Ser Ala Phe Cys Phe Leu Ser His Asp His Gly Arg Thr Trp Ala Arg
        195                 200                 205

Gly His Phe Val Ala Gln Asp Thr Leu Glu Cys Gln Val Ala Glu Val
210                 215                 220

Glu Thr Gly Glu Gln Arg Val Val Thr Leu Asn Ala Arg Ser His Leu
225                 230                 235                 240

Arg Ala Arg Val Gln Ala Gln Ser Thr Asn Asp Gly Leu Asp Phe Gln
                245                 250                 255

Glu Ser Gln Leu Val Lys Lys Leu Val Glu Pro Pro Gln Gly Cys
            260                 265                 270

Gln Gly Ser Val Ile Ser Phe Pro Ser Pro Arg Ser Gly Pro Gly Ser
        275                 280                 285

Pro Gln Trp Leu Leu Tyr Thr His Pro Thr His Ser Trp Gln Arg Ala
            290                 295                 300

```
Asp Leu Gly Ala Tyr Leu Asn Pro Arg Pro Ala Pro Glu Ala Trp
305                 310                 315                 320

Ser Glu Pro Val Leu Leu Ala Lys Gly Ser Cys Ala Tyr Ser Asp Leu
                325                 330                 335

Gln Ser Met Gly Thr Gly Pro Asp Gly Ser Pro Leu Phe Gly Cys Leu
            340                 345                 350

Tyr Glu Ala Asn Asp Tyr Glu Ile Val Phe Leu Met Phe Thr Leu
        355                 360                 365

Lys Gln Ala Phe Pro Ala Glu Tyr Leu Pro Gln
    370                 375

<210> SEQ ID NO 9
<211> LENGTH: 424
<212> TYPE: PRT
<213> ORGANISM: Homo sapiens

<400> SEQUENCE: 9

Leu Ala Gly Gly Ser Val Arg Trp Gly Ala Leu His Val Leu Gly Thr
1               5                   10                  15

Ala Ala Leu Ala Glu His Arg Ser Met Asn Pro Cys Pro Val His Asp
                20                  25                  30

Ala Gly Thr Gly Thr Val Phe Leu Phe Ile Ala Val Leu Gly His
            35                  40                  45

Thr Pro Glu Ala Val Gln Ile Ala Thr Gly Arg Asn Ala Ala Arg Leu
    50                  55                  60

Cys Cys Val Ala Ser Arg Asp Ala Gly Leu Ser Trp Gly Ser Ala Arg
65                  70                  75                  80

Asp Leu Thr Glu Glu Ala Ile Gly Gly Ala Val Gln Asp Trp Ala Thr
                85                  90                  95

Phe Ala Val Gly Pro Gly His Gly Val Gln Leu Pro Ser Gly Arg Leu
            100                 105                 110

Leu Val Pro Ala Tyr Thr Tyr Arg Val Asp Arg Leu Glu Cys Phe Gly
        115                 120                 125

Lys Ile Cys Arg Thr Ser Pro His Ser Phe Ala Phe Tyr Ser Asp Asp
130                 135                 140

His Gly Arg Thr Trp Arg Cys Gly Gly Leu Val Pro Asn Leu Arg Ser
145                 150                 155                 160

Gly Glu Cys Gln Leu Ala Ala Val Asp Gly Gly Gln Ala Gly Ser Phe
                165                 170                 175

Leu Tyr Cys Asn Ala Arg Ser Pro Leu Gly Ser Arg Val Gln Ala Leu
            180                 185                 190

Ser Thr Asp Glu Gly Thr Ser Phe Leu Pro Ala Glu Arg Val Ala Ser
        195                 200                 205

Leu Pro Glu Thr Ala Trp Gly Cys Gln Gly Ser Ile Val Gly Phe Pro
    210                 215                 220

Ala Pro Ala Pro Asn Arg Pro Arg Asp Ser Trp Ser Val Gly Pro
225                 230                 235                 240

Arg Ser Pro Leu Gln Pro Leu Leu Gly Pro Gly Val His Glu Pro
                245                 250                 255

Pro Glu Glu Ala Ala Val Asp Pro Arg Gly Gly Gln Val Pro Gly Gly
            260                 265                 270

Pro Phe Ser Arg Leu Gln Pro Arg Gly Asp Gly Pro Arg Gln Pro Gly
        275                 280                 285

Pro Arg Pro Gly Val Ser Gly Asp Val Gly Ser Trp Thr Leu Ala Leu
    290                 295                 300
```

```
Pro Met Pro Phe Ala Ala Pro Pro Gln Ser Pro Thr Trp Leu Leu Tyr
305                 310                 315                 320

Ser His Pro Val Gly Arg Arg Ala Arg Leu His Met Gly Ile Arg Leu
                325                 330                 335

Ser Gln Ser Pro Leu Asp Pro Arg Ser Trp Thr Glu Pro Trp Val Ile
            340                 345                 350

Tyr Glu Gly Pro Ser Gly Tyr Ser Asp Leu Ala Ser Ile Gly Pro Ala
        355                 360                 365

Pro Glu Gly Gly Leu Val Phe Ala Cys Leu Tyr Glu Ser Gly Ala Arg
    370                 375                 380

Thr Ser Tyr Asp Glu Ile Ser Phe Cys Thr Phe Ser Leu Arg Glu Val
385                 390                 395                 400

Leu Glu Asn Val Pro Ala Ser Pro Lys Pro Pro Asn Leu Gly Asp Lys
                405                 410                 415

Pro Arg Gly Cys Cys Trp Pro Ser
            420

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Gly Gly Gly Gly Ser
1               5

<210> SEQ ID NO 11
<211> LENGTH: 2742
<212> TYPE: DNA
<213> ORGANISM: Actinomyces viscosus
<220> FEATURE:
<223> OTHER INFORMATION: nanH gene for sialidase

<400> SEQUENCE: 11
atgacatcgc atagtccttt ctcccggagg cgcctgccgg ccctcctggg ctccctgcca      60
ctggccgcca ccggcctgat cgccgccgca ccccggcgc acgccgtccc cacgtctgac     120
ggcctggccg acgtcaccat cacgcaggtg aacgcgcccg cggacggcct ctactccgtc     180
ggcgatgtca tgaccttcaa catcaccctg accaacacca gcggcgaggc ccactcctac     240
gccccggcct cgacgaacct gtccgggaac gtctccaagt gccggtggcg caacgtcccg     300
gccgggacga ccaagaccga ctgcaccggc ctggccacgc acacggtgac cgccgaggac     360
ctcaaggccg gtggcttcac cccgcagatc gcctacgagg tcaaggccgt ggagtacgcc     420
gggaaggccc tgagcacccc ggagacgatc aagggcgcga cgagcccagt caaggccaac     480
tcgctgcggg tcgagtcgat cacgccgtcg tcgagccagg agaactacaa gctgggcgac     540
accgtcagct acacggtgcg cgtgcgctcg gtgtcggaca agacgatcaa cgtcgccgcc     600
accgaatcct ccttcgacga cctgggccgc cagtgccact ggggcggcct caagccgggc     660
aagggcgccc tctacaactg caagccgctc acccacacga tcacgcaagc cgacgtcgac     720
gccggccgct ggacgccatc gatcaccctg acggccaccg gaaccgacgg cgccaccctc     780
cagacgctca ccgccaccgg caaccgatc aacgtcgtcg cgaccacccc gcaggccacg     840
cccgcaccgg cgcccgacgc gagcacggag ctgccggcct caatgagcca ggcccagcac     900
ctggccgcca acacggccac cgacaactac cgcatcccgg cgataccacc gcccccaatg     960
```

-continued

```
gggacctgct catctcctac gacgagcgcc cgaaggacaa cggcaacggc ggcagcgacg    1020
acccccaacc cgaaccacat cgtccagcgc cgctccaccg acggcggcaa gacctggtcg    1080
gcgcccacct acatccacca gggcacggag accggcaaga aggtcggcta ctccgacccg    1140
agctacgtcg tcgatcacca gacgggcacg atcttcaact ccacgtcaa gtcctacgac     1200 cagggctggg gcggctcgcg cggcggcacc gacccggaga accggggcat catccaggcc    1260
gaggtgtcga cctccacgga caacggctgg acctggacgc accgcacgat cccgcggac    1320 atcacgaagg acaagccgtg gaccgcgcgt tcgcggcct cgggccaggg catccagatt    1380
cagcacgggc cccacgccgg gcgcctggtg cagcagtaca cgatcaggac cgccggcggg    1440
ccggtgcagg ccgtctcggt ctactccgac gaccacggga agacgtggca ggccggcacg    1500
ccgatcggga ccggcatgga tgagaacaag gtcgttgagc tctccgacgg ctccctcatg    1560
ctcaactcgc gcgcctcgga tggctccggc ttccgcaagg tggcccactc caccgacggt    1620
gggcagacct ggagcgagcc ggtgtccgac aagaacctgc ccgactcggt ggacaacgcc    1680
cagatcatcc gagccttccc gaacgccgcg ccggacgacc cgcgcgccaa ggtgctgctg    1740
ctgagccact caccgaaccc gcggccgtgg tgccgtgacc gcggcaccat ctcgatgtcc    1800
tgcgacgacg gcgcctcctg gacgaccagc aaggtcttcc acgagccctt cgtcggatac    1860
acgacgatcg cggtgcagtc cgacggcagc atcgggctgc tcagcgagga cgcccacaac    1920
ggcgccgact acggcggcat ctggtaccgc aacttcacga tgaactggct cggcgagcag    1980
tgcggccaga gccggcgga gccgagcccg gccgtcgcc gacggcggca ccctcagcgg     2040
caccgacgga gaagccggcc ccgtcggccg cgccgagcgc tgagcccacg caggcaccgg    2100
caccatcctc cgcgcccgag ccgagcgctg cgcccgagcc gagcaggccc cggcgccgga    2160
gcccacgacc gctccgagca cggagcccac accggctcct gcgcccagtc cgcacctgag    2220
cagaccgatg gccgaccgc tgcgcccgca ccggagacgt cctctgcacc ggccgccgaa     2280
ccgacgcagg ccccgacggt ggcgccttct gttgagccca cgcaggctcc gggtgcgcag    2340
ccgagctcag cacccaagcc ggggggcgacg ggtcgggccc cgtcggtggt gaacccgaag    2400
gcgaccgggg cggcgacgga gcctgggacg ccgtcatcga gcgcgagccc ggcaccgagc    2460
cggaacgcgg cgccgacgcc gaagccgggc atggagcccg atgagattga tcggccgtct    2520
gacggcacca tggcgcagcc gaccggtgcg ccagcgcgcc gagtgccgcg ccgacgcagg    2580
cggcgaaggc cggcagcagg ctgtctcgca cgggaccaac gcgctgctga tcctgggcct    2640
tgcgggtgtc gcggttgtcg gcgggtacct gctgctgcgg gctcgccgtt cgaagaactg    2700
aacacgcgac gagccggtca tccggctctg agcactgact ga                       2742
```

<210> SEQ ID NO 12
<211> LENGTH: 913
<212> TYPE: PRT
<213> ORGANISM: Actinomyces viscosus
<220> FEATURE:
<223> OTHER INFORMATION: nanH sialidase

<400> SEQUENCE: 12

Met Thr Ser His Ser Pro Phe Ser Arg Arg Arg Leu Pro Ala Leu Leu
1               5                   10                  15

Gly Ser Leu Pro Leu Ala Ala Thr Gly Leu Ile Ala Ala Pro Pro
            20                  25                  30

Ala His Ala Val Pro Thr Ser Asp Gly Leu Ala Asp Val Thr Ile Thr
        35                  40                  45

```
Gln Val Asn Ala Pro Ala Asp Gly Leu Tyr Ser Val Gly Asp Val Met
     50                  55                  60

Thr Phe Asn Ile Thr Leu Thr Asn Thr Ser Gly Glu Ala His Ser Tyr
 65                  70                  75                  80

Ala Pro Ala Ser Thr Asn Leu Ser Gly Asn Val Ser Lys Cys Arg Trp
                 85                  90                  95

Arg Asn Val Pro Ala Gly Thr Lys Thr Asp Cys Thr Gly Leu Ala
                100                 105                 110

Thr His Thr Val Thr Ala Glu Asp Leu Lys Ala Gly Phe Thr Pro
             115                 120                 125

Gln Ile Ala Tyr Glu Val Lys Ala Val Glu Tyr Ala Gly Lys Ala Leu
        130                 135                 140

Ser Thr Pro Glu Thr Ile Lys Gly Ala Thr Ser Pro Val Lys Ala Asn
145                 150                 155                 160

Ser Leu Arg Val Glu Ser Ile Thr Pro Ser Ser Gln Glu Asn Tyr
                165                 170                 175

Lys Leu Gly Asp Thr Val Ser Tyr Thr Val Arg Val Arg Ser Val Ser
            180                 185                 190

Asp Lys Thr Ile Asn Val Ala Ala Thr Glu Ser Ser Phe Asp Asp Leu
        195                 200                 205

Gly Arg Gln Cys His Trp Gly Gly Leu Lys Pro Gly Lys Gly Ala Val
    210                 215                 220

Tyr Asn Cys Lys Pro Leu Thr His Thr Ile Thr Gln Ala Asp Val Asp
225                 230                 235                 240

Ala Gly Arg Trp Thr Pro Ser Ile Thr Leu Thr Ala Thr Gly Thr Asp
                245                 250                 255

Gly Ala Thr Leu Gln Thr Leu Thr Ala Thr Gly Asn Pro Ile Asn Val
            260                 265                 270

Val Gly Asp His Pro Gln Ala Thr Pro Ala Pro Ala Pro Asp Ala Ser
        275                 280                 285

Thr Glu Leu Pro Ala Ser Met Ser Gln Ala Gln His Leu Ala Ala Asn
    290                 295                 300

Thr Ala Thr Asp Asn Tyr Arg Ile Pro Ala Ile Pro Pro Pro Met
305                 310                 315                 320

Gly Thr Cys Ser Ser Pro Thr Thr Ser Ala Arg Arg Thr Thr Ala Thr
                325                 330                 335

Ala Ala Ala Thr Thr Pro Asn Pro Asn His Ile Val Gln Arg Arg Ser
            340                 345                 350

Thr Asp Gly Gly Lys Thr Trp Ser Ala Pro Thr Tyr Ile His Gln Gly
        355                 360                 365

Thr Glu Thr Gly Lys Lys Val Gly Tyr Ser Asp Pro Ser Tyr Val Val
    370                 375                 380

Asp His Gln Thr Gly Thr Ile Phe Asn Phe His Val Lys Ser Tyr Asp
385                 390                 395                 400

Gln Gly Trp Gly Gly Ser Arg Gly Gly Thr Asp Pro Glu Asn Arg Gly
                405                 410                 415

Ile Ile Gln Ala Glu Val Ser Thr Ser Thr Asp Asn Gly Trp Thr Trp
            420                 425                 430

Thr His Arg Thr Ile Thr Ala Asp Ile Thr Lys Asp Lys Pro Trp Thr
        435                 440                 445

Ala Arg Phe Ala Ala Ser Gly Gln Gly Ile Gln Ile Gln His Gly Pro
    450                 455                 460
```

```
His Ala Gly Arg Leu Val Gln Gln Tyr Thr Ile Arg Thr Ala Gly Gly
465                 470                 475                 480

Pro Val Gln Ala Val Ser Val Tyr Ser Asp Asp His Gly Lys Thr Trp
            485                 490                 495

Gln Ala Gly Thr Pro Ile Gly Thr Gly Met Asp Glu Asn Lys Val Val
            500                 505                 510

Glu Leu Ser Asp Gly Ser Leu Met Leu Asn Ser Arg Ala Ser Asp Gly
            515                 520                 525

Ser Gly Phe Arg Lys Val Ala His Ser Thr Asp Gly Gln Thr Trp
530                 535                 540

Ser Glu Pro Val Ser Asp Lys Asn Leu Pro Asp Ser Val Asp Asn Ala
545                 550                 555                 560

Gln Ile Ile Arg Ala Phe Pro Asn Ala Ala Pro Asp Asp Pro Arg Ala
                565                 570                 575

Lys Val Leu Leu Leu Ser His Ser Pro Asn Pro Arg Pro Trp Cys Arg
                580                 585                 590

Asp Arg Gly Thr Ile Ser Met Ser Cys Asp Asp Gly Ala Ser Trp Thr
            595                 600                 605

Thr Ser Lys Val Phe His Glu Pro Phe Val Gly Tyr Thr Thr Ile Ala
610                 615                 620

Val Gln Ser Asp Gly Ser Ile Gly Leu Leu Ser Glu Asp Ala His Asn
625                 630                 635                 640

Gly Ala Asp Tyr Gly Gly Ile Trp Tyr Arg Asn Phe Thr Met Asn Trp
                645                 650                 655

Leu Gly Glu Gln Cys Gly Gln Lys Pro Ala Glu Pro Ser Pro Gly Arg
            660                 665                 670

Arg Arg Arg Arg His Pro Gln Arg His Arg Arg Ser Arg Pro Arg
            675                 680                 685

Arg Pro Arg Arg Ala Leu Ser Pro Arg Arg His Arg His His Pro Pro
            690                 695                 700

Arg Pro Ser Arg Ala Leu Arg Pro Ser Arg Ala Gly Pro Gly Ala Gly
705                 710                 715                 720

Ala His Asp Arg Ser Glu His Gly Ala His Thr Gly Ser Cys Ala Gln
                725                 730                 735

Ser Ala Pro Glu Gln Thr Asp Gly Pro Thr Ala Ala Pro Ala Pro Glu
            740                 745                 750

Thr Ser Ser Ala Pro Ala Ala Glu Pro Thr Gln Ala Pro Thr Val Ala
            755                 760                 765

Pro Ser Val Glu Pro Thr Gln Ala Pro Gly Ala Gln Pro Ser Ser Ala
            770                 775                 780

Pro Lys Pro Gly Ala Thr Gly Arg Ala Pro Ser Val Val Asn Pro Lys
785                 790                 795                 800

Ala Thr Gly Ala Ala Thr Glu Pro Gly Thr Pro Ser Ser Ser Ala Ser
            805                 810                 815

Pro Ala Pro Ser Arg Asn Ala Ala Pro Thr Pro Lys Pro Gly Met Glu
            820                 825                 830

Pro Asp Glu Ile Asp Arg Pro Ser Asp Gly Thr Met Ala Gln Pro Thr
            835                 840                 845

Gly Ala Pro Ala Arg Arg Val Pro Arg Arg Arg Arg Arg Pro
            850                 855                 860

Ala Ala Gly Cys Leu Ala Arg Asp Gln Arg Ala Ala Asp Pro Gly Pro
865                 870                 875                 880

Cys Gly Cys Arg Gly Cys Arg Arg Val Pro Ala Ala Ala Gly Ser Pro
```

```
                    885                 890                 895
Phe Glu Glu Leu Asn Thr Arg Arg Ala Gly His Pro Ala Leu Ser Thr
                900                 905                 910

Asp

<210> SEQ ID NO 13
<211> LENGTH: 443
<212> TYPE: PRT
<213> ORGANISM: Artificial Sequence
<220> FEATURE:
<223> OTHER INFORMATION: Synthetic Construct

<400> SEQUENCE: 13

Val Lys Arg Lys Lys Gly Gly Lys Asn Gly Lys Asn Arg Arg Asn
1               5                   10                  15

Arg Lys Lys Lys Asn Pro Gly Asp His Pro Gln Ala Thr Pro Ala Pro
                20                  25                  30

Ala Pro Asp Ala Ser Thr Glu Leu Pro Ala Ser Met Ser Gln Ala Gln
            35                  40                  45

His Leu Ala Ala Asn Thr Ala Thr Asp Asn Tyr Arg Ile Pro Ala Ile
        50                  55                  60

Thr Thr Ala Pro Asn Gly Asp Leu Leu Ile Ser Tyr Asp Glu Arg Pro
65                  70                  75                  80

Lys Asp Asn Gly Asn Gly Gly Ser Asp Ala Pro Asn Pro Asn His Ile
                85                  90                  95

Val Gln Arg Arg Ser Thr Asp Gly Gly Lys Thr Trp Ser Ala Pro Thr
            100                 105                 110

Tyr Ile His Gln Gly Thr Glu Thr Gly Lys Lys Val Gly Tyr Ser Asp
        115                 120                 125

Pro Ser Tyr Val Val Asp His Gln Thr Gly Thr Ile Phe Asn Phe His
    130                 135                 140

Val Lys Ser Tyr Asp Gln Gly Trp Gly Gly Ser Arg Gly Gly Thr Asp
145                 150                 155                 160

Pro Glu Asn Arg Gly Ile Ile Gln Ala Glu Val Ser Thr Ser Thr Asp
                165                 170                 175

Asn Gly Trp Thr Trp Thr His Arg Thr Ile Thr Ala Asp Ile Thr Lys
            180                 185                 190

Asp Lys Pro Trp Thr Ala Arg Phe Ala Ala Ser Gly Gln Gly Ile Gln
        195                 200                 205

Ile Gln His Gly Pro His Ala Gly Arg Leu Val Gln Gln Tyr Thr Ile
    210                 215                 220

Arg Thr Ala Gly Gly Ala Val Gln Ala Val Ser Val Tyr Ser Asp Asp
225                 230                 235                 240

His Gly Lys Thr Trp Gln Ala Gly Thr Pro Ile Gly Thr Gly Met Asp
                245                 250                 255

Glu Asn Lys Val Val Glu Leu Ser Asp Gly Ser Leu Met Leu Asn Ser
            260                 265                 270

Arg Ala Ser Asp Gly Ser Gly Phe Arg Lys Val Ala His Ser Thr Asp
        275                 280                 285

Gly Gly Gln Thr Trp Ser Glu Pro Val Ser Asp Lys Asn Leu Pro Asp
    290                 295                 300

Ser Val Asp Asn Ala Gln Ile Ile Arg Ala Phe Pro Asn Ala Ala Pro
305                 310                 315                 320

Asp Asp Pro Arg Ala Lys Val Leu Leu Leu Ser His Ser Pro Asn Pro
                325                 330                 335
```

```
Arg Pro Trp Ser Arg Asp Arg Gly Thr Ile Ser Met Ser Cys Asp Asp
                340                 345                 350

Gly Ala Ser Trp Thr Thr Ser Lys Val Phe His Glu Pro Phe Val Gly
            355                 360                 365

Tyr Thr Thr Ile Ala Val Gln Ser Asp Gly Ser Ile Gly Leu Leu Ser
        370                 375                 380

Glu Asp Ala His Asn Gly Ala Asp Tyr Gly Gly Ile Trp Tyr Arg Asn
385                 390                 395                 400

Phe Thr Met Asn Trp Leu Gly Glu Gln Cys Gly Gln Lys Pro Ala Glu
                405                 410                 415

Gly Ala Asp Tyr Gly Gly Ile Trp Tyr Arg Asn Phe Thr Met Asn Trp
            420                 425                 430

Leu Gly Glu Gln Cys Gly Gln Lys Pro Ala Glu
        435                 440

<210> SEQ ID NO 14
<211> LENGTH: 444
<212> TYPE: PRT
<213> ORGANISM: Artificial Sequence
<220> FEATURE:
<223> OTHER INFORMATION: Synthetic Construct

<400> SEQUENCE: 14

Met Val Lys Arg Lys Lys Gly Gly Lys Asn Gly Lys Asn Arg Arg
1               5                   10                  15

Asn Arg Lys Lys Lys Asn Pro Gly Asp His Pro Gln Ala Thr Pro Ala
                20                  25                  30

Pro Ala Pro Asp Ala Ser Thr Glu Leu Pro Ala Ser Met Ser Gln Ala
            35                  40                  45

Gln His Leu Ala Ala Asn Thr Ala Thr Asp Asn Tyr Arg Ile Pro Ala
        50                  55                  60

Ile Thr Thr Ala Pro Asn Gly Asp Leu Leu Ile Ser Tyr Asp Glu Arg
65                  70                  75                  80

Pro Lys Asp Asn Gly Asn Gly Gly Ser Asp Ala Pro Asn Pro Asn His
                85                  90                  95

Ile Val Gln Arg Arg Ser Thr Asp Gly Gly Lys Thr Trp Ser Ala Pro
                100                 105                 110

Thr Tyr Ile His Gln Gly Thr Glu Thr Gly Lys Lys Val Gly Tyr Ser
            115                 120                 125

Asp Pro Ser Tyr Val Val Asp His Gln Thr Gly Thr Ile Phe Asn Phe
        130                 135                 140

His Val Lys Ser Tyr Asp Gln Gly Trp Gly Gly Ser Arg Gly Gly Thr
145                 150                 155                 160

Asp Pro Glu Asn Arg Gly Ile Ile Gln Ala Glu Val Ser Thr Ser Thr
                165                 170                 175

Asp Asn Gly Trp Thr Trp Thr His Arg Thr Ile Thr Ala Asp Ile Thr
            180                 185                 190

Lys Asp Lys Pro Trp Thr Ala Arg Phe Ala Ala Ser Gly Gln Gly Ile
        195                 200                 205

Gln Ile Gln His Gly Pro His Ala Gly Arg Leu Val Gln Gln Tyr Thr
    210                 215                 220

Ile Arg Thr Ala Gly Gly Ala Val Gln Ala Val Ser Val Tyr Ser Asp
225                 230                 235                 240

Asp His Gly Lys Thr Trp Gln Ala Gly Thr Pro Ile Gly Thr Gly Met
                245                 250                 255
```

```
Asp Glu Asn Lys Val Val Glu Leu Ser Asp Gly Ser Leu Met Leu Asn
            260                 265                 270

Ser Arg Ala Ser Asp Gly Ser Phe Arg Lys Val Ala His Ser Thr
        275                 280                 285

Asp Gly Gly Gln Thr Trp Ser Glu Pro Val Ser Asp Lys Asn Leu Pro
    290                 295                 300

Asp Ser Val Asp Asn Ala Gln Ile Ile Arg Ala Phe Pro Asn Ala Ala
305                 310                 315                 320

Pro Asp Asp Pro Arg Ala Lys Val Leu Leu Leu Ser His Ser Pro Asn
                325                 330                 335

Pro Arg Pro Trp Ser Arg Asp Arg Gly Thr Ile Ser Met Ser Cys Asp
            340                 345                 350

Asp Gly Ala Ser Trp Thr Thr Ser Lys Val Phe His Glu Pro Phe Val
        355                 360                 365

Gly Tyr Thr Thr Ile Ala Val Gln Ser Asp Gly Ser Ile Gly Leu Leu
    370                 375                 380

Ser Glu Asp Ala His Asn Gly Ala Asp Tyr Gly Gly Ile Trp Tyr Arg
385                 390                 395                 400

Asn Phe Thr Met Asn Trp Leu Gly Glu Gln Cys Gly Gln Lys Pro Ala
                405                 410                 415

Glu Gly Ala Asp Tyr Gly Gly Ile Trp Tyr Arg Asn Phe Thr Met Asn
            420                 425                 430

Trp Leu Gly Glu Gln Cys Gly Gln Lys Pro Ala Glu
        435                 440

<210> SEQ ID NO 15
<211> LENGTH: 415
<212> TYPE: PRT
<213> ORGANISM: Artificial Sequence
<220> FEATURE:
<223> OTHER INFORMATION: Synthetic construct

<400> SEQUENCE: 15

Met Gly Asp His Pro Gln Ala Thr Pro Ala Pro Ala Pro Asp Ala Ser
1               5                   10                  15

Thr Glu Leu Pro Ala Ser Met Ser Gln Ala Gln His Leu Ala Ala Asn
            20                  25                  30

Thr Ala Thr Asp Asn Tyr Arg Ile Pro Ala Ile Thr Thr Ala Pro Asn
        35                  40                  45

Gly Asp Leu Leu Ile Ser Tyr Asp Glu Arg Pro Lys Asp Asn Gly Asn
    50                  55                  60

Gly Gly Ser Asp Ala Pro Asn Pro Asn His Ile Val Gln Arg Arg Ser
65                  70                  75                  80

Thr Asp Gly Gly Lys Thr Trp Ser Ala Pro Thr Tyr Ile His Gln Gly
                85                  90                  95

Thr Glu Thr Gly Lys Lys Val Gly Tyr Ser Asp Pro Ser Tyr Val Val
            100                 105                 110

Asp His Gln Thr Gly Thr Ile Phe Asn Phe His Val Lys Ser Tyr Asp
        115                 120                 125

Gln Gly Trp Gly Gly Ser Arg Gly Gly Thr Asp Pro Glu Asn Arg Gly
    130                 135                 140

Ile Ile Gln Ala Glu Val Ser Thr Ser Thr Asp Asn Gly Trp Thr Trp
145                 150                 155                 160

Thr His Arg Thr Ile Thr Ala Asp Ile Thr Lys Asp Lys Pro Trp Thr
                165                 170                 175
```

```
Ala Arg Phe Ala Ala Ser Gly Gln Gly Ile Gln Ile Gln His Gly Pro
            180                 185                 190

His Ala Gly Arg Leu Val Gln Gln Tyr Thr Ile Arg Thr Ala Gly Gly
        195                 200                 205

Ala Val Gln Ala Val Ser Val Tyr Ser Asp Asp His Gly Lys Thr Trp
210                 215                 220

Gln Ala Gly Thr Pro Ile Gly Thr Gly Met Asp Glu Asn Lys Val Val
225                 230                 235                 240

Glu Leu Ser Asp Gly Ser Leu Met Leu Asn Ser Arg Ala Ser Asp Gly
                245                 250                 255

Ser Gly Phe Arg Lys Val Ala His Ser Thr Asp Gly Gln Thr Trp
            260                 265                 270

Ser Glu Pro Val Ser Asp Lys Asn Leu Pro Asp Ser Val Asp Asn Ala
            275                 280                 285

Gln Ile Ile Arg Ala Phe Pro Asn Ala Ala Pro Asp Asp Pro Arg Ala
        290                 295                 300

Lys Val Leu Leu Leu Ser His Ser Pro Asn Pro Arg Pro Trp Ser Arg
305                 310                 315                 320

Asp Arg Gly Thr Ile Ser Met Ser Cys Asp Asp Gly Ala Ser Trp Thr
                325                 330                 335

Thr Ser Lys Val Phe His Glu Pro Phe Val Gly Tyr Thr Thr Ile Ala
            340                 345                 350

Val Gln Ser Asp Gly Ser Ile Gly Leu Leu Ser Glu Asp Ala His Asn
        355                 360                 365

Gly Ala Asp Tyr Gly Gly Ile Trp Tyr Arg Asn Phe Thr Met Asn Trp
370                 375                 380

Leu Gly Glu Gln Cys Gly Gln Lys Pro Ala Lys Arg Lys Lys Lys Gly
385                 390                 395                 400

Gly Lys Asn Gly Lys Asn Arg Arg Asn Arg Lys Lys Asn Pro
                405                 410                 415

<210> SEQ ID NO 16
<211> LENGTH: 414
<212> TYPE: PRT
<213> ORGANISM: Artificial Sequence
<220> FEATURE:
<223> OTHER INFORMATION: Synthetic construct

<400> SEQUENCE: 16

Gly Asp His Pro Gln Ala Thr Pro Ala Pro Ala Pro Asp Ala Ser Thr
1               5                   10                  15

Glu Leu Pro Ala Ser Met Ser Gln Ala Gln His Leu Ala Ala Asn Thr
            20                  25                  30

Ala Thr Asp Asn Tyr Arg Ile Pro Ala Ile Thr Thr Ala Pro Asn Gly
        35                  40                  45

Asp Leu Leu Ile Ser Tyr Asp Glu Arg Pro Lys Asp Asn Gly Asn Gly
    50                  55                  60

Gly Ser Asp Ala Pro Asn Pro Asn His Ile Val Gln Arg Arg Ser Thr
65                  70                  75                  80

Asp Gly Gly Lys Thr Trp Ser Ala Pro Thr Tyr Ile His Gln Gly Thr
                85                  90                  95

Glu Thr Gly Lys Lys Val Gly Tyr Ser Asp Pro Ser Tyr Val Val Asp
            100                 105                 110

His Gln Thr Gly Thr Ile Phe Asn Phe His Val Lys Ser Tyr Asp Gln
        115                 120                 125
```

-continued

```
Gly Trp Gly Gly Ser Arg Gly Gly Thr Asp Pro Glu Asn Arg Gly Ile
    130                 135                 140

Ile Gln Ala Glu Val Ser Thr Ser Thr Asp Asn Gly Trp Thr Trp Thr
145                 150                 155                 160

His Arg Thr Ile Thr Ala Asp Ile Thr Lys Asp Lys Pro Trp Thr Ala
                165                 170                 175

Arg Phe Ala Ala Ser Gly Gln Gly Ile Gln Ile Gln His Gly Pro His
            180                 185                 190

Ala Gly Arg Leu Val Gln Gln Tyr Thr Ile Arg Thr Ala Gly Gly Ala
        195                 200                 205

Val Gln Ala Val Ser Val Tyr Ser Asp Asp His Gly Lys Thr Trp Gln
    210                 215                 220

Ala Gly Thr Pro Ile Gly Thr Gly Met Asp Glu Asn Lys Val Val Glu
225                 230                 235                 240

Leu Ser Asp Gly Ser Leu Met Leu Asn Ser Arg Ala Ser Asp Gly Ser
                245                 250                 255

Gly Phe Arg Lys Val Ala His Ser Thr Asp Gly Gly Gln Thr Trp Ser
            260                 265                 270

Glu Pro Val Ser Asp Lys Asn Leu Pro Asp Ser Val Asp Asn Ala Gln
        275                 280                 285

Ile Ile Arg Ala Phe Pro Asn Ala Ala Pro Asp Asp Pro Arg Ala Lys
    290                 295                 300

Val Leu Leu Leu Ser His Ser Pro Asn Pro Arg Pro Trp Ser Arg Asp
305                 310                 315                 320

Arg Gly Thr Ile Ser Met Ser Cys Asp Asp Gly Ala Ser Trp Thr Thr
                325                 330                 335

Ser Lys Val Phe His Glu Pro Phe Val Gly Tyr Thr Thr Ile Ala Val
            340                 345                 350

Gln Ser Asp Gly Ser Ile Gly Leu Leu Ser Glu Asp Ala His Asn Gly
        355                 360                 365

Ala Asp Tyr Gly Gly Ile Trp Tyr Arg Asn Phe Thr Met Asn Trp Leu
    370                 375                 380

Gly Glu Gln Cys Gly Gln Lys Pro Ala Lys Arg Lys Lys Lys Gly Gly
385                 390                 395                 400

Lys Asn Gly Lys Asn Arg Arg Asn Arg Lys Lys Lys Asn Pro
                405                 410
```